(12) United States Patent
Guevremont et al.

(10) Patent No.: US 7,265,347 B2
(45) Date of Patent: Sep. 4, 2007

(54) MULTIPLE NANO-SPRAY DELIVERY SYSTEM FOR FAIMS

(75) Inventors: Roger Guevremont, Ottawa (CA); Govindanunny Thekkadath, Ottawa (CA); James T. Kapron, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 184 days.

(21) Appl. No.: 11/130,124

(22) Filed: May 17, 2005

(65) Prior Publication Data

US 2005/0258359 A1 Nov. 24, 2005

Related U.S. Application Data

(60) Provisional application No. 60/572,117, filed on May 19, 2004.

(51) Int. Cl.
*B01D 59/44* (2006.01)
(52) U.S. Cl. ............... 250/287; 250/283; 250/286; 250/281; 250/282; 250/292
(58) Field of Classification Search ............... 250/287, 250/288, 286, 282, 292
See application file for complete search history.

(56) References Cited

U.S. PATENT DOCUMENTS

| | | | |
|---|---|---|---|
| 5,420,424 A | 5/1995 | Carnahan et al. | |
| 6,504,149 B2 | 1/2003 | Guevremont et al. | |
| 6,690,004 B2 | 2/2004 | Miller et al. | |
| 6,753,522 B2 * | 6/2004 | Guevremont et al. | ....... 250/287 |
| 7,034,286 B2 * | 4/2006 | Guevremont et al. | ....... 250/282 |
| 2003/0111599 A1 | 6/2003 | Staats | |
| 2003/0230711 A1 * | 12/2003 | Guevremont et al. | ....... 250/287 |
| 2004/0206902 A1 | 10/2004 | Staats | |
| 2004/0232326 A1 * | 11/2004 | Guevremont et al. | ....... 250/287 |
| 2005/0194532 A1 * | 9/2005 | Guevremont et al. | ....... 250/294 |

* cited by examiner

*Primary Examiner*—Robert Kim
*Assistant Examiner*—Johnnie L Smith, II
(74) *Attorney, Agent, or Firm*—Freedman & Associates

(57) ABSTRACT

An apparatus for multiple nano-spray delivery of a sample to FAIMS analyzer includes a micro-machined ionization source having a plurality of discrete nozzles. At least some of the discrete nozzles of the plurality are aligned one each with an ion inlet of a plurality of discrete ion inlets of the FAIMS, so that ions produced at different discrete nozzles are introduced into different portions of the FAIMS analyzer region. The ions that are introduced via each ion inlet are at least partly separated prior to adding/mixing with the ions introduced via other ion inlets. This reduces the problems of ion-ion electric repulsions that occur when ion density is high.

23 Claims, 14 Drawing Sheets

MULTIPLE NANO-SPRAY DELIVERY SYSTEM FOR FAIMS

This application claims benefit from U.S. Provisional application 60/572,117 filed on May 19, 2004.

FIELD OF THE INVENTION

The instant invention relates generally to high field asymmetric waveform ion mobility spectrometry (FAIMS). In particular, the instant invention relates to an apparatus and method for multiple nano-spray delivery of a sample to FAIMS.

BACKGROUND

Atmospheric pressure ionization sources are widely used to study ions of biological interest. One of the most widely used sources is electrospray ionization, in which the liquid is delivered to the tip of a needle that is held at high voltage relative to some counter-electrode. The strong field around the tip of the needle serves to atomize the liquid, to charge the droplets and to push ions formed in the spray towards the counter electrode. Many names are applied to this technology including nanospray, nanoelectrospray, picospray, and turboionspray as some non-limiting examples of this class of ionization source. When coupled to this type of atmospheric pressure ionization source, a mass spectrometer, specifically a vacuum chamber of a mass spectrometer, generally has only a single opening to atmospheric pressure. Additional openings are not very practical for two reasons: (i) the introduction of a higher flow of gas into the vacuum system requires higher vacuum pumping capability, and (ii) combining the ions flowing through two or more openings is difficult inside the vacuum chamber of the mass spectrometer. The single opening into the mass spectrometer makes the delivery of ions from two or more ionization sources problematic, although several methods have been proposed and utilized.

Since FAIMS operates at atmospheric pressure, the option of utilizing multiple inlets is more readily exploited. Some examples of apparatus and methods associated with delivering the ions from several ion sources have been described in previous patent applications, such as for example U.S. Provisional Application No. 60/505,868, the contents of which are incorporated herein by reference.

Previously, multiple ion inlet FAIMS systems have been designed for maximizing the efficiency of operation of the mass spectrometer. For example U.S. Pat. No. 6,753,522 issued Jun. 22, 2004 in the name of Guevremont et al., the contents of which is incorporated herein by reference, teaches providing the sample flow from two separate flow injection systems to two independent ionization sources, which are then multiplexed into FAIMS through two ports. The selection of an active port is achieved by mechanical or electronic selection, with the objective being to deliver ions from each source during a period of time in which the alternative or non-active source cannot deliver sample (i.e. the alternative source is between samples). In this way the mass spectrometer is utilized more efficiently, with less time spent waiting for the next useful sample to be delivered. In another example, one of the ion sources is used for the calibration of the mass scale of a high-resolution mass spectrometer. The reference compound is delivered occasionally via one of the ion sources to periodically refresh the mass calibration.

It would be advantageous to increase the sensitivity of the mass spectrometer measurement by delivering a higher flow of ions through FAIMS. For example, this may be accomplished using several ionization sources that are arranged in parallel, all of which are ionizing the same sample. Normally this has not been done because the effort that is required to operate two sources is significant. In addition, since the mass spectrometer has only one opening, providing ions from several sources is not very practical nor does it provide higher sensitivity. This is because, under normal circumstances, additional ion sources mean that each source must necessarily be located further from the single opening into the mass spectrometer. As a result, each source is coupled less effectively and the ion flux from a given source into the mass spectrometer is lower than it would be if the ion source were located in an optimal position adjacent to the ion inlet into the mass spectrometer.

SUMMARY OF THE INVENTION

According to an aspect of the instant invention, provided is an apparatus for separating ions, comprising: a first electrode; a second electrode that is spaced-apart from the first electrode so as to define a FAIMS analyzer region therebetween, the FAIMS analyzer region including a plurality of ion inlets defined through the first electrode for supporting fluid communication between the analyzer region and a region that is external to the analyzer region; a micro-machined ionization source disposed within the region that is external to the analyzer region and including a plurality of spaced-apart nozzles, each nozzle of the plurality of spaced-apart nozzles being aligned approximately with an ion inlet of the plurality of ion inlets; and, at least an electrical controller for applying an asymmetric waveform voltage and a direct current compensation voltage between the first electrode and the second electrode so as to generate an electrical field therebetween, and for applying a voltage for inducing ionization of a liquid sample that is provided to the micro-machined ionization source, wherein, during use, ions are provided simultaneously to different portions of the analyzer region via different ion inlets of the plurality of ion inlets, the ions provided through each ion inlet being produced substantially at a nozzle that is aligned approximately with that ion inlet.

According to another aspect of the instant invention, provided is an apparatus for separating ions, comprising: an ionization source comprising a substrate defining a plurality of discrete nozzles, each discrete nozzle having a first end for receiving a liquid sample including a species of interest, a second end for providing a flow of a fluid including ions of the species of interest, and a passageway defined through the substrate and extending between the first end and the second end for conducting the liquid sample between the first end and the second end; an electrical contact on the ionization source for receiving an electrical signal, the electrical signal for use in producing ions from the liquid sample that is contained within the passageways of at least some of the plurality of discrete nozzles; and, a FAIMS analyzer comprising an analyzer region defined between two spaced-apart electrodes and including an ion outlet and a plurality of ion inlets, each ion inlet of the plurality of ion inlets being defined at a different distance from the ion outlet such that, during use, a mixture of ions introduced via a first ion inlet is partially separated prior to mixing with a mixture of ions introduced via a second ion inlet that is disposed between the first ion inlet and the ion outlet.

According to another aspect of the instant invention, provided is an apparatus for separating ions, comprising: an ionizer comprising a monolithic substrate defining a plurality of discrete ionization sources that are disposed in a predetermined spaced-apart arrangement; a FAIMS analyzer comprising an analyzer region defined between two spaced-apart electrodes and including an ion outlet and a plurality of ion inlets, the plurality of ion inlets being arranged in the predetermined spaced-apart arrangement, such that each ion inlet is aligned with one of the plurality of discrete ionization sources when in an assembled condition; and, an electrical contact on the ionizer for receiving an electrical signal for initiating ionization of a liquid sample that is provided to the ionizer, so as to provide simultaneously ions from each of the plurality of discrete ionization sources.

According to another aspect of the instant invention, provided is a method for separating ions, comprising: providing a FAIMS analyzer region defined between a first electrode and a second electrode; applying an asymmetric waveform voltage and a direct current compensation voltage between the first electrode and the second electrode to generate an electric field within the analyzer region; providing a liquid sample to each of a plurality of discrete nozzles of an ionizer; applying a voltage to the ionizer for effecting ionization of the liquid sample at each discrete nozzle, to produce ions of species that are contained within the liquid sample; during a same overlapping period of time, introducing ions produced at each discrete nozzle through a corresponding ion inlet of a plurality of ion inlets into the FAIMS analyzer region, such that ions produced at each discrete nozzle are introduced into a different volume of the FAIMS analyzer region via a different ion inlet of the plurality of ion inlets; and, selectively transmitting ions of a same type introduced through each ion inlet of the plurality of ion inlets toward a same ion outlet from the FAIMS analyzer region, such that ions introduced via different ion inlets have different residence times within the FAIMS analyzer region.

BRIEF DESCRIPTION OF THE DRAWINGS

Exemplary embodiments of the invention will now be described in conjunction with the accompanying drawings, in which.

DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1:
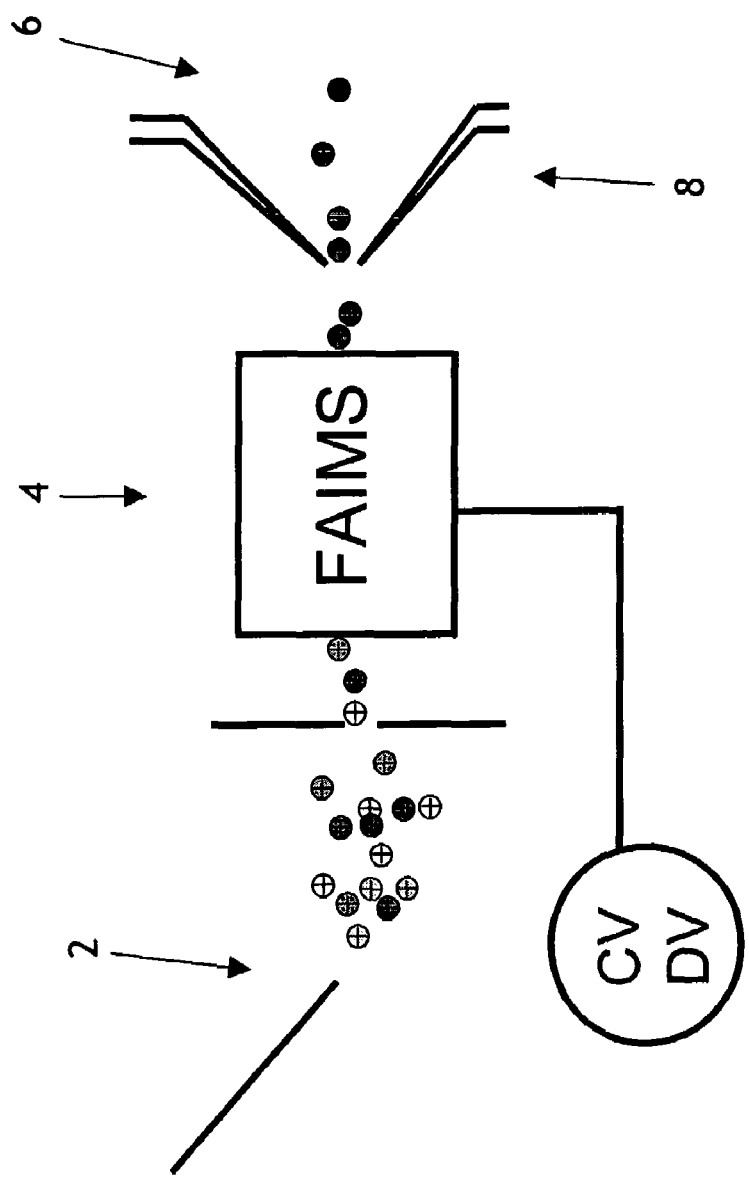
FIG. 1 shows a prior art tandem arrangement of an ion source, a FAIMS system, and an ion detection system.

FIG. 1 illustrates a prior art tandem arrangement of an ion source 2, a FAIMS system 4, and an ion detection system 6 in the form of a mass spectrometer. The ion source 2 is shown in the form of an electrospray ionizer, but equally suitable ion sources include photoionization sources, atmospheric pressure MALDI, radioactivity-based sources, corona discharge sources, or other rf-based discharge sources as some non-limiting examples. The FAIMS system 4 is used to separate ions prior to introduction of the ions to the sampling cone 8 of the vacuum chamber of the mass spectrometer 6. It is an advantage of FAIMS that the signal-to-background ratio is significantly improved, and that in some cases isomeric and isobaric ions are separated.

Figure 2:
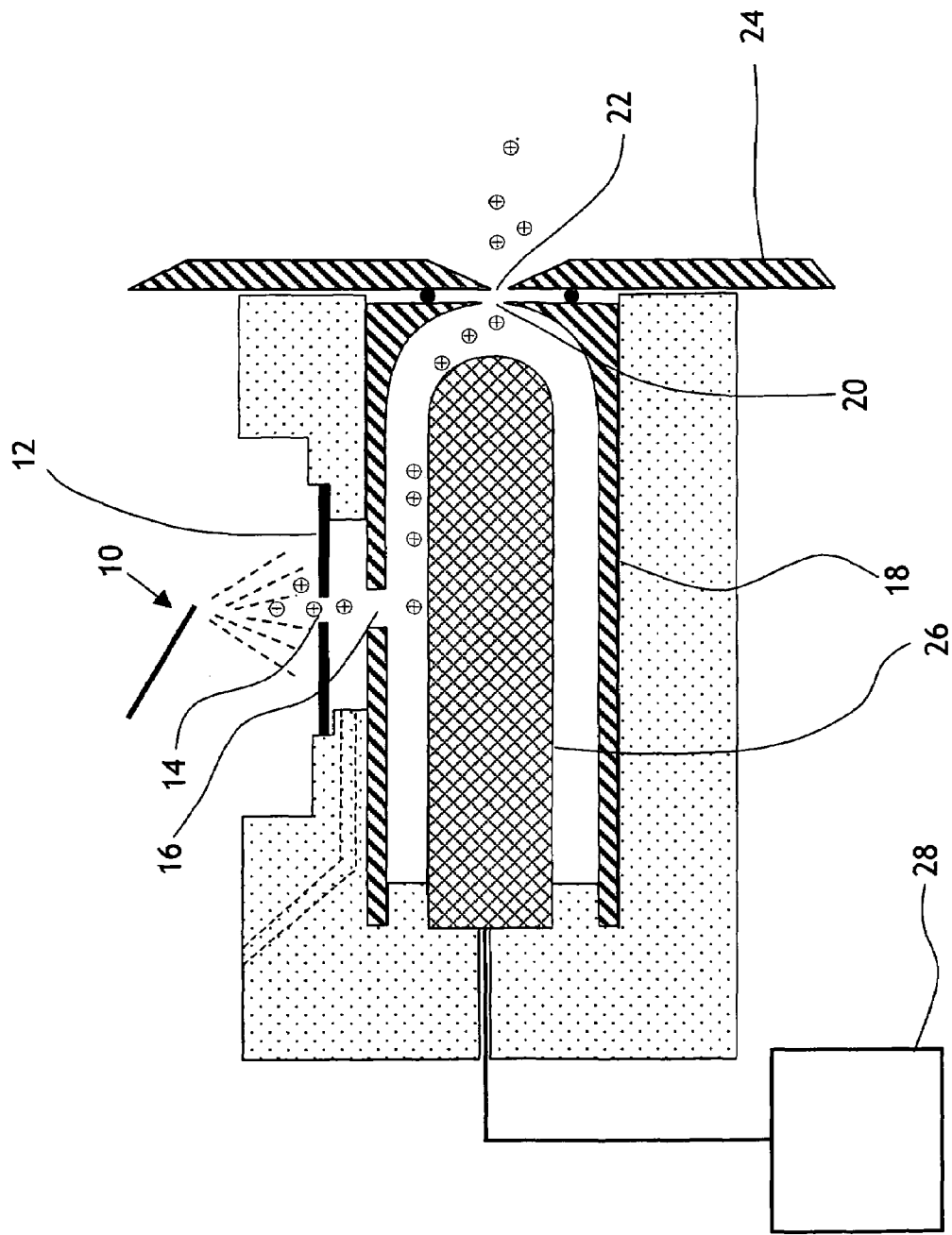
FIG. 2 is a schematic diagram of one possible prior art arrangement for combining an electrospray ionization source with a FAIMS system.

FIG. 2 illustrates schematically one prior art arrangement for combining electrospray ionization with one non-limiting example of a FAIMS system. In FIG. 2 the ions are formed near the tip of the electrospray needle 10 and drift towards the curtain plate 12. The curtain gas, which is introduced below the curtain plate 12, divides into two flows. One of the two flows exits through a curtain plate aperture 14 in the curtain plate 12 to prevent neutrals and droplets from entering the curtain plate aperture 14. Ions are driven against this gas by a voltage gradient from the electrospray needle 10 to the curtain plate 12. Ions that pass through the curtain plate aperture 14 in the curtain plate 12 are further pushed towards the ion inlet 16 of FAIMS by a field generated between the curtain plate 12 and the outer FAIMS electrode 18. The other of the two flows of the curtain gas passes through the ion inlet 16 and carries the ions along the length of the FAIMS electrodes to an ion outlet 20, and then into a not illustrated ion detection system, such as for instance a mass spectrometer, via an orifice 22 in orifice plate 24.

During use, a high voltage asymmetric waveform is applied to the inner electrode 26 of FAIMS by an electrical controller 28 via at least an electrical contact on the FAIMS inner electrode 26. Fields generated from this applied voltage cause the ions to oscillate between the inner electrode 26 and the outer electrode 18. The high voltage asymmetric waveform is generated so as to cause the ions to move in a first direction in a strong field for a short time, followed by motion in the other direction in a weaker field for a longer time. Absent any change in ion mobility between the high field and low field portions of this applied high voltage asymmetric waveform, the ion is expected to return to its original position relative to the surface of the electrodes after each cycle of the waveform, if the effects of diffusion or ion-ion repulsion are not considered. In practice however, the mobility of many ions is different in strong and weak electric fields. Hence, after one cycle of the high voltage asymmetric waveform the ions do not return to their starting position relative to the electrode surfaces. A second voltage, a dc voltage called the compensation voltage, is applied to eliminate this change of position. The compensation voltage is set to a value that causes the ion to travel equal distances relative to the surface of the electrodes in the positive and negative phases of the waveform. In other words, the compensation voltage is set to eliminate, or compensate for, the change of position that a particular ion species would exhibit under the influence of one cycle of the high voltage asymmetric waveform. Therefore, ions of the particular ion species for which the compensation voltage is set return to the same location relative to the electrodes after each cycle of the high voltage asymmetric waveform. These ions do not migrate towards one or the other electrode and are transmitted through FAIMS. Other ions, for which the compensation voltage is either too high or too low, drift toward an electrode and are not transmitted through FAIMS.

Figure 3:
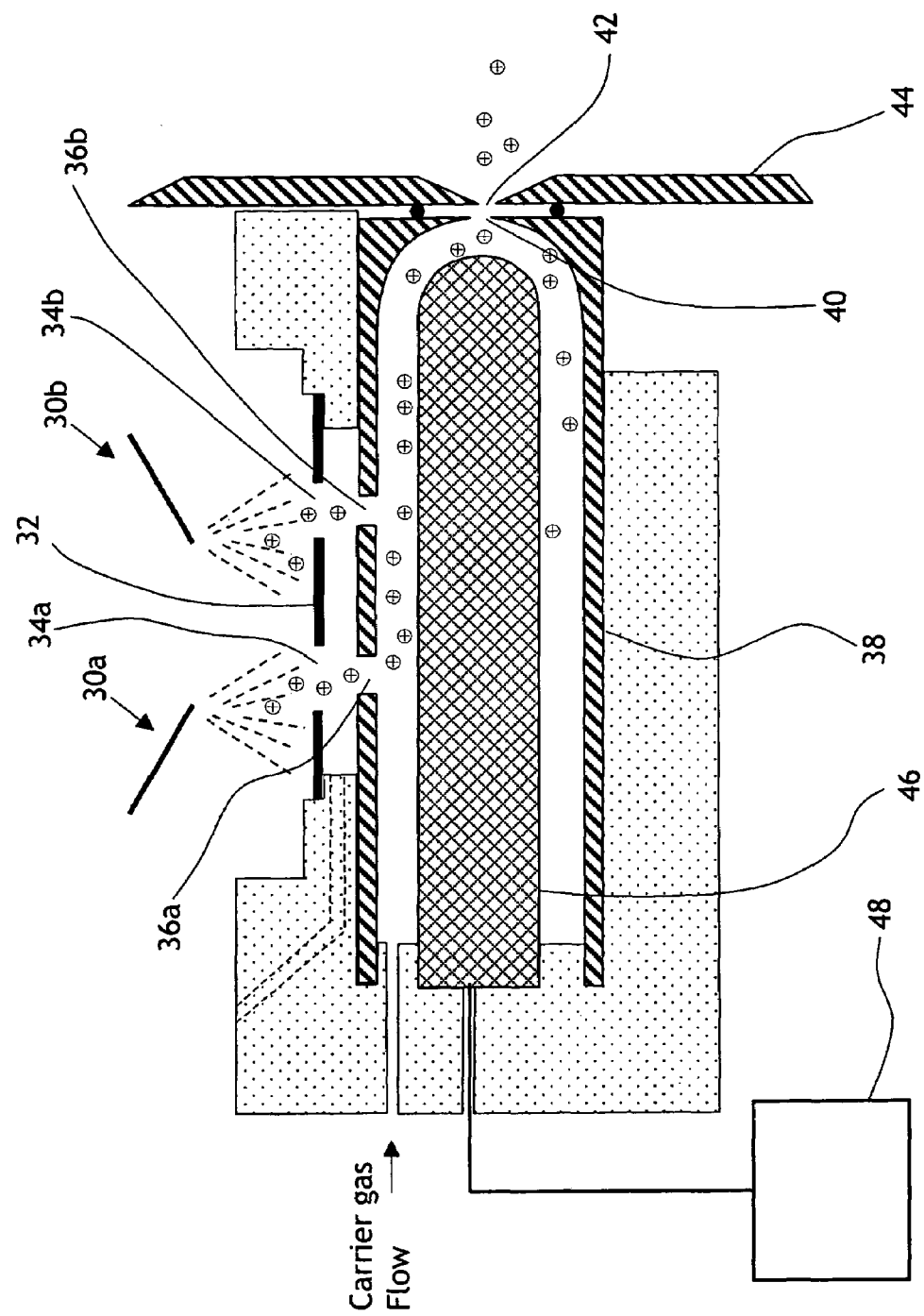
FIG. 3 is a schematic diagram of one possible arrangement for combining a plurality of separate ionization sources with a FAIMS system.

FIG. 3 illustrates schematically one arrangement for combining a plurality of separate ionization sources with one non-limiting example of a FAIMS system. In FIG. 3 the ions are formed near the tip of the electrospray needle 30a and near the tip of the electrospray needle 30b. Although electrospray ionization sources are shown by way of a specific and non-limiting example, optionally another suitable ionization source is used instead. The ions that are formed drift towards the curtain plate 32, which has two openings 34a and 34b defined therethrough. In particular, the opening 34a is aligned with the electrospray needle 30a and the opening 34b is aligned with the electrospray needle 30b. A portion of the curtain gas, which is introduced below the curtain plate 32, exits through the openings 34a and 34b in the curtain plate 32 to prevent neutrals and droplets from entering through the openings 34a and 34b, respectively. Ions are driven against this outward flow of gas by a voltage gradient from the electrospray needle 30a or 30b to the curtain plate 32. Ions that pass through the aperture 34a or 34b in the curtain plate 32 are further pushed towards an ion inlet 36a or 36b of FAIMS by a field generated between the curtain plate 32 and the outer FAIMS electrode 38. A second portion of the curtain gas flows through the ion inlet 36a or 36b and carries the ions along the length of the FAIMS electrodes to an ion outlet 40, and then into a not illustrated ion detection system, such as for instance a mass spectrometer, via an orifice 42 in orifice plate 44. During use, a high voltage asymmetric waveform and direct current compensation voltage is applied to the inner electrode 46 of FAIMS by an electrical controller 48 via at least an electrical contact on the FAIMS inner electrode 46.

In the system of FIG. 3, ions from both ionization sources 30a and 30b enter FAIMS. If the ionizers are both provided with the same sample, the FAIMS is used to separate the ions of interest from background and/or other interfering compounds and the ions of interest from both sources are combined into a single stream for delivery into the orifice of the mass spectrometer. Optionally the system shown in FIG. 3 is modified to accommodate many parallel ionizers arranged around the circumference of FAIMS.

Two unexpected benefits are observed using the system of FIG. 3. First, despite any limitations in the efficiency of producing an analyte ion by the ionizer, twice the number of ions of interest is produced since the two ionizers operate in parallel, i.e. simultaneously and with a same sample. In some cases the ionizer is made more efficient by delivery of a lower flow of sample and, therefore, such parallel operation results in higher analyte ion production efficiency than a single ionizer working with twice the liquid flow. This system therefore effectively provides the benefits of higher liquid sample flows and takes advantage of the benefits of delivering the smallest possible liquid flow to each of the electrospray (or nano-spray, or pico-spray etc.) ionizers. Secondly, it is an unexpected benefit that the ions from a source are at least partly separated prior to adding/mixing with the ions from other sources. This reduces the problems of ion-ion electric repulsions that occur when ion density is high. The FAIMS of this system is used to isolate the analyte ions, i.e. the ions of interest, from a high abundance of other ions prior to combining the ion flows for delivery to the mass spectrometer. This benefit cannot be had if the same total ion production arrived in FAIMS from a single ion source and/or through a single ion inlet.

On the other hand, the multiple openings in the curtain plate and the multiple ion inlets of FAIMS act to divide the total curtain gas flow into a greater number of smaller gas flows. Since the curtain gas is used to deliver ions from the region between the curtain plate and the outer FAIMS electrode into each of the ion inlets of FAIMS, the total curtain gas flow is split into several portions, or gas flows, exiting this region. The curtain gas also flows out of this region towards each of the independent ionizers through respective opening in the curtain plate. Preferably, the transport of ions from each source into the FAIMS is optimized to require a minimum of total curtain gas flow. Optionally, a carrier gas flow is provided directly to the analyzer region between the inner and outer electrodes, in a manner shown in FIG. 3, to transport the ions along FAIMS. The total gas flow through FAIMS is controlled by the rate of flow of gas being pulled through the orifice of the mass spectrometer. This gas flow is composed of the sum of the carrier gas flow and the flows of curtain gas into the ion inlets.

Of course, a user assembles multiple independent ionization sources to operate the system shown in FIG. 3, and the same sample is provided independently to each of the ionization sources.

Figure 4:
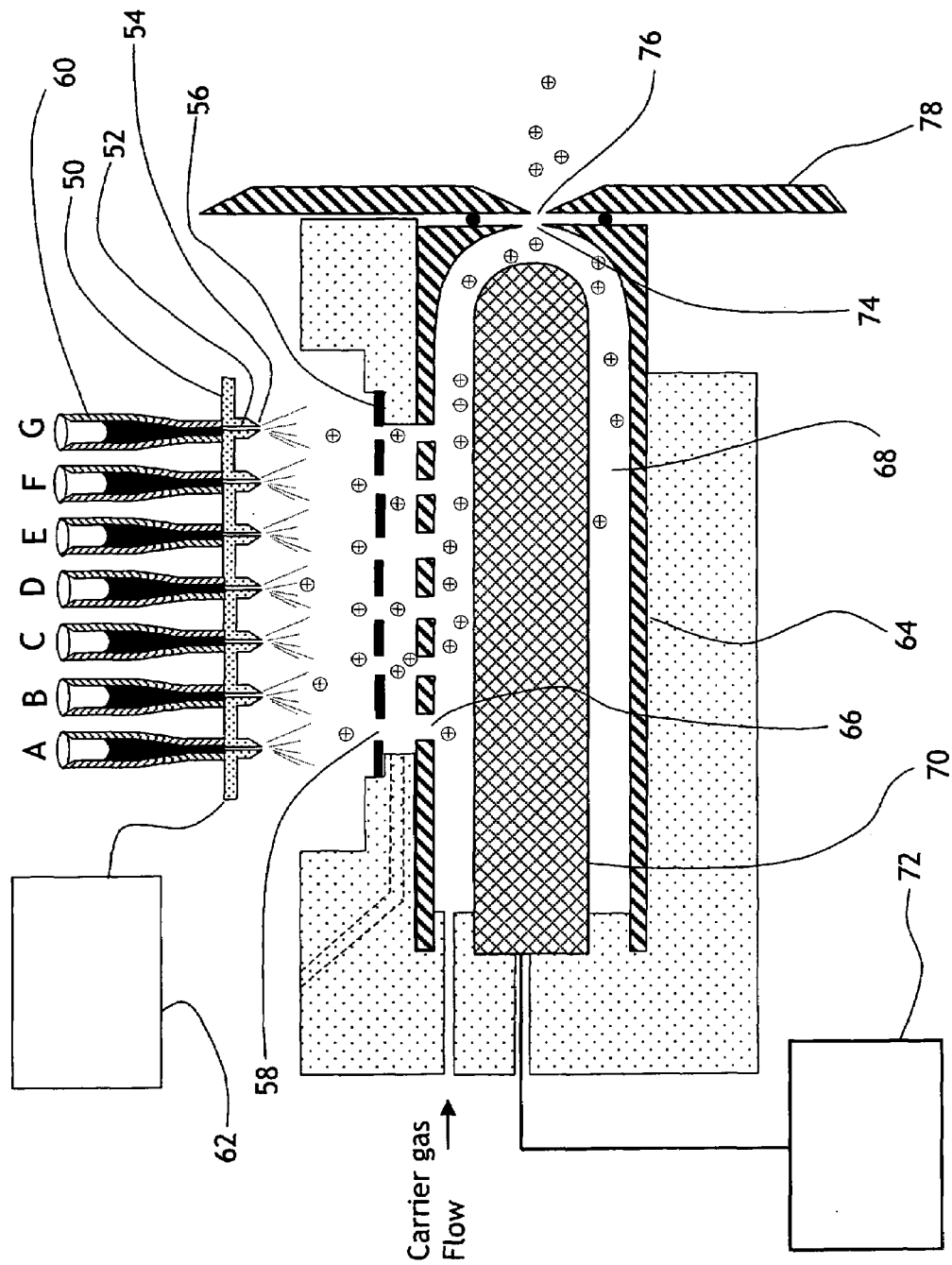
FIG. 4 is a schematic diagram of an automated multiple sample spray system coupled with a FAIMS system.

FIG. 4 illustrates an automated multiple spray system according to an embodiment of the instant invention. A micro-machined ionization source, for instance an electrospray wafer 50, preferably a monolithic silicon substrate including a plurality of small capillaries 52 and protruding tips 54 that are adequate to induce an electrospray process, is disposed adjacent to and spaced-apart from a curtain plate 56 of FAIMS. The small capillaries 52 and protruding tips 54 will also be referred to in this document simply as nozzles.

A plurality of openings 58 is defined through the curtain plate 56, such that one opening of the plurality is aligned with one protruding tip 54 of the electrospray wafer 50. FIG. 4 also illustrates that, during use, a sample loader including a plurality of disposable pipettes 60, or another suitable type of sample transfer vessel, is positioned for delivering fluid sample to the back side of the electrospray wafer 50. The liquid sample is optionally pushed out of the disposable pipettes 60 by gas pressure, and/or drawn by capillary action into the capillaries 52 in the electrospray wafer 50. An electrical controller 62 is used to apply a voltage to the electrospray wafer 50 and/or to the liquid samples via a not illustrated electrical contact, so that the liquid is caused to spray out of the plurality of protruding tips 54 along the front side of the electrospray wafer 50. The ions thus produced are driven by an electric field towards the curtain plate 56. A portion of the curtain gas, which is introduced below the curtain plate 56, exits through the plurality of openings 58 in the curtain plate 56 to prevent neutrals and droplets from entering through the curtain plate openings. A voltage difference between the curtain plate 56 and a FAIMS outer electrode 64 directs the ions toward a plurality of ion inlets 66 defined through the FAIMS outer electrode 64. Some of the curtain gas flows through the ion inlets 66 and carries the ions into the space 68 between a FAIMS inner electrode 70 and the FAIMS outer electrode 64. During use, a high voltage asymmetric waveform and direct current compensation voltage is applied to the FAIMS inner electrode 70 by an electrical controller 72 via at least an electrical contact on the FAIMS inner electrode 70. Optionally, the electrical controller 62 and the electrical controller 72 are integrated within a same electrical controller unit. The ions are separated within the space 68, also referred to as the analyzer region, as they are carried by a flow of gas towards an ion outlet 74 and then into a not illustrated ion detection system, such as for instance a mass spectrometer via an orifice 76 in orifice plate 78, for detection and/or additional analysis. Of course, optionally the detection of ions is done by other means including measurement of the electrical current using an electrometer or faraday cup, or by laser-based methods described elsewhere, as some non-limiting examples. The system is not uniquely suited to mass spectrometry, but optionally is used with any other ion detection system. However, it is known that detection by mass spectrometry is sensitive and provides specificity in the identification of the ions by determining their mass to charge ratio.

The system shown in FIG. 4 solves many of the problems that are inherent with systems such as that shown in FIG. 3. The plurality of electrospray nozzles, each nozzle including one of the small capillaries 52 and one associated protruding tip 54, does not require individual preparation, because all of the nozzles of the plurality are mounted on a same silicon wafer chip. Since the nozzles are only used for one sample, each one is highly likely to perform correctly during this single operation, and accordingly the nozzles do not suffer from degradation over many uses nor from problems of clogging or buildup of salts. These problems are known limitations of fixed electrospray needles of the type that is shown in the previous figures.

The system shown in FIG. 4 also provides a simple approach to deliver the same sample through multiple electrospray nozzles. The loading of the series of disposable pipettes is readily automated with existing technology.

Referring still to FIG. 4, it is an advantage that the ions that are produced at different nozzles are introduced into different portions of the FAIMS analyzer region. For instance, the left-most pipette is labeled "A" in FIG. 4, and the right-most pipette is labeled "G," with the intermediate pipettes being referred to from left to right as "B," "C," "D," "E," and "F," respectively. Ions produced at the nozzle that is associated with pipette "A," including ions of interest and "background ions" are introduced through the left-most inlet of the FAIMS outer electrode. Upon entering the analyzer region 68, the background ions begin to collide with the electrode surfaces and are lost, assuming appropriate conditions for selectively transmitting only the ions of interest are present. A flow of a carrier gas "sweeps" the ions from left to right in FIG. 4, such that surviving ions introduced at the left most inlet of the FAIMS outer electrode are carried into other portions of the FAIMS analyzer region where ions are being introduced from one of the other nozzles, such as for instance nozzle "B." The ion density resulting from the presence of surviving ions introduced at the left most inlet and from the presence of ions introduced at the inlet that is aligned with nozzle "B" is lower than it would be if the ions from nozzle "A" and from nozzle "B" were introduced through a same inlet. This is because at least partial separation or removal of background ions has occurred between the time the ions are introduced at the left most inlet, and the time that the ions arrive at the portion of the analyzer region at which the ions from nozzle "B" are being introduced. Accordingly, space-charge repulsion and other inter-ion forces are reduced using the system shown at FIG. 4, compared to a system in which an equal volume of sample, and assuming an approximately equal number of ions, is introduced from a single ion source into a FAIMS analyzer region via a single inlet. By reducing the effects of space-charge repulsion caused by abundance of background ions, fewer ions of interest collide with the electrodes and a relatively higher proportion of the available ions is detected. This reduction of ion density of background ions leads to improved sensitivity for the ion of interest.

Figure 5:
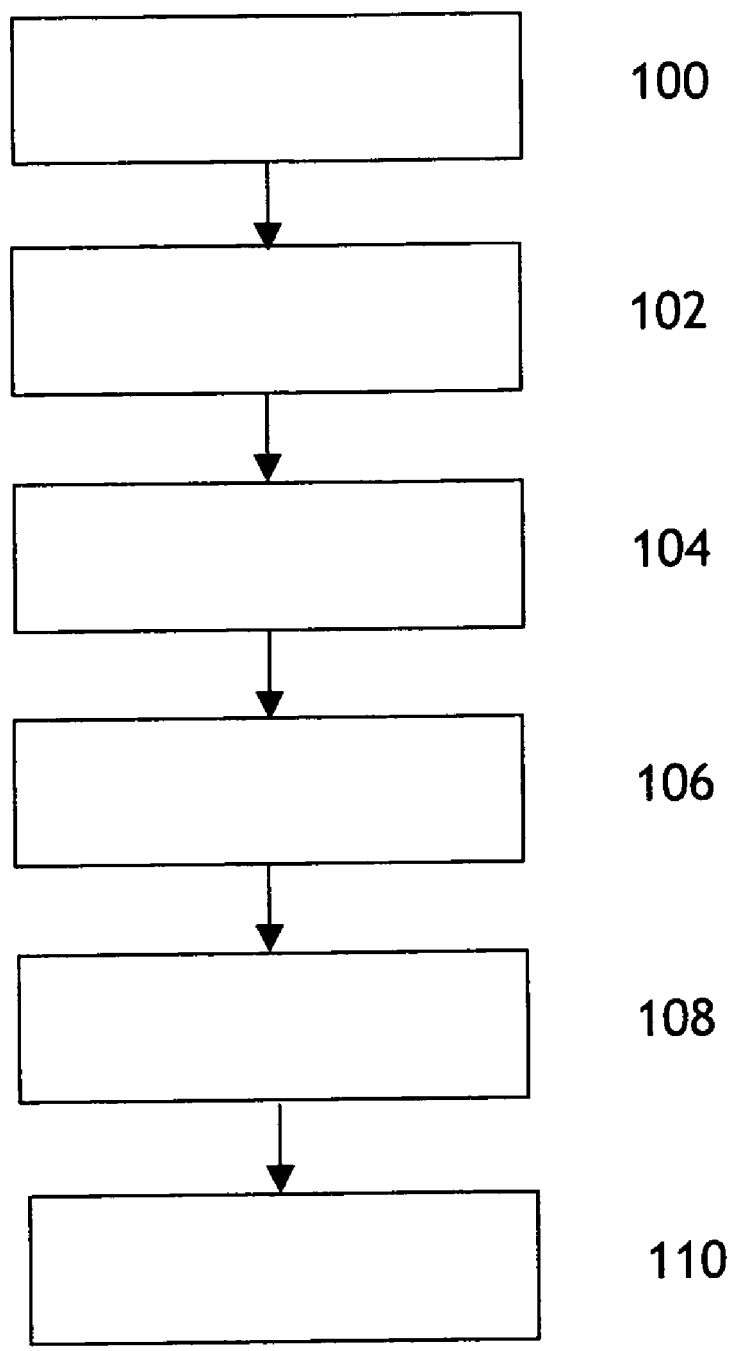
FIG. 5 is a simplified flow diagram of a method according to an embodiment of the instant invention.

FIG. 5 is a simplified flow diagram of a method according to an embodiment of the instant invention. At step 100, a FAIMS analyzer region defined between a first electrode and a second electrode is provided. At step 102, an asymmetric waveform voltage and a direct current compensation voltage is applied between the first electrode and the second electrode, so as to generate an electric field within the analyzer region. The combination of asymmetric waveform voltage and direct current compensation voltage is selected in dependence upon other operating parameters and the identity of the ions of interest to be separated. At step 104, a liquid sample is provided to each of a plurality of discrete nozzles of an ionizer. For instance, disposable pipettes are filled with a liquid sample and each pipette is positioned adjacent to a back surface of the ionizer for providing the liquid sample to a discrete nozzle of the ionizer. At step 106, a voltage is applied to the ionizer via an electrical contact, for effecting ionization of the liquid sample at each discrete nozzle, to produce ions of species that are contained within the liquid sample. At step 108, during a same overlapping period of time, ions produced at each discrete nozzle are introduced through a corresponding ion inlet of a plurality of ion inlets into the FAIMS analyzer region, such that ions produced at each discrete nozzle are introduced into a different volume of the FAIMS analyzer region via a different ion inlet of the plurality of ion inlets. At step 110, ions of a same type introduced through each ion inlet of the plurality of ion inlets are selectively transmitted toward a same ion outlet from the FAIMS analyzer region, such that ions introduced via different ion inlets have different residence times within the FAIMS analyzer region.

Figure 6:
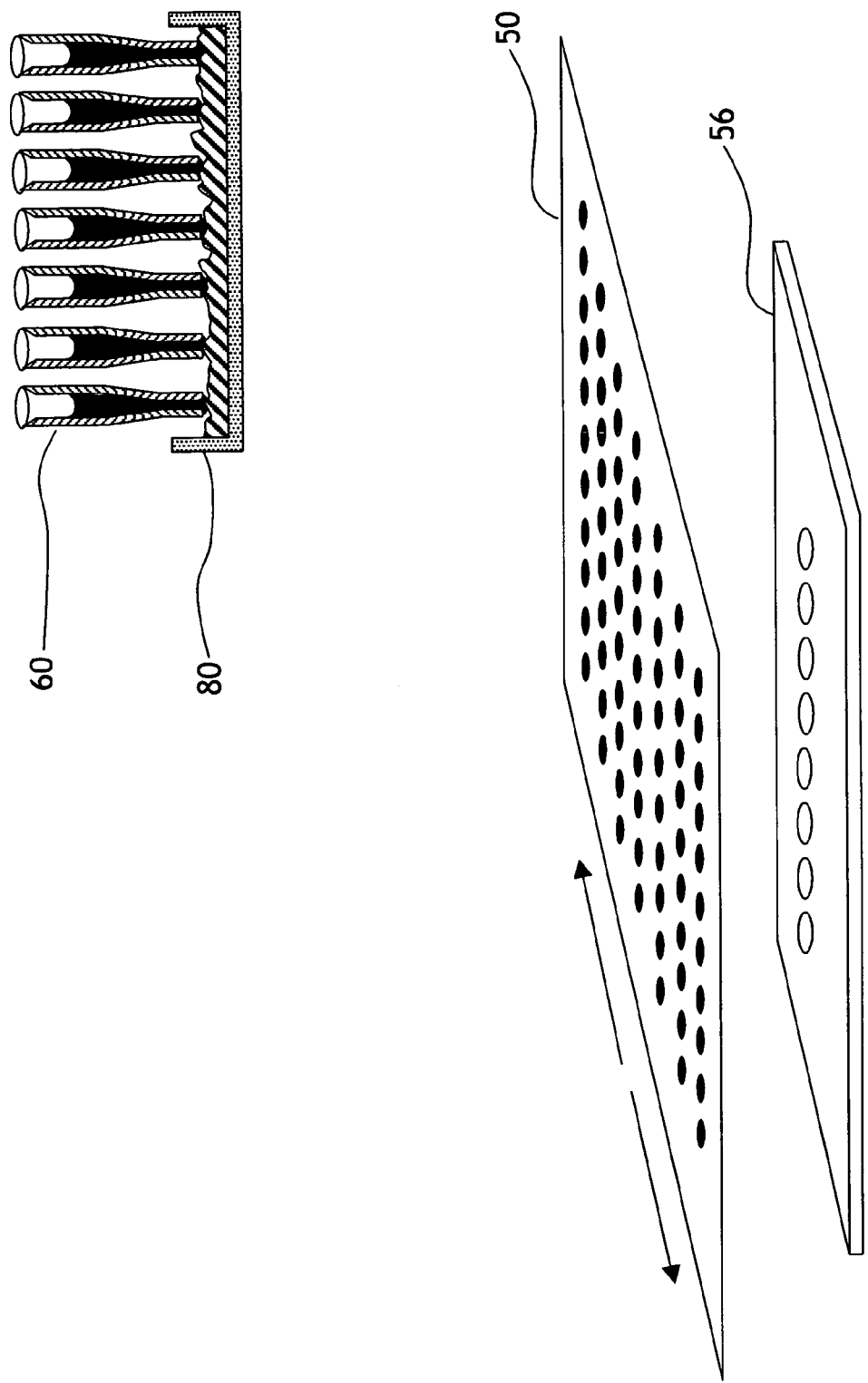
FIG. 6 is a simplified schematic diagram illustrating a first step of a method according to an embodiment of the instant invention.

FIGS. 6 to 10 illustrate the step-wise manner in which the system of FIG. 4 is operated. FIG. 6 illustrates, in a very simplified and schematic way, the multi-hole curtain plate 56 of FAIMS with a plurality of openings for transmitting the ions from a source which, in this embodiment, includes a silicon wafer with a plurality of electrospray nozzles, into the curtain gas region and into FAIMS. The electrospray wafer 50, in the form of a silicon wafer with a plurality of electrospray nozzles, is shown. The plurality of electrospray nozzles includes a plurality of rows of electrospray nozzles. A not illustrated mechanism, similar to an "x-y stage," is provided for translating the electrospray nozzle 50 in the direction of the arrows shown in the figure. In this way, each of the rows of electrospray nozzles is aligned with the plurality of openings in sequence. In FIG. 6, a sample loader including a set of disposable pipette tips 60, or another suitable type of sample transfer vessel, is shown collecting a portion of sample from a sample reservoir 80. Although a single reservoir 80 is shown here, each pipette tip 60 optionally collects sample from a different sample well. Optionally each pipette collects sample from a single well if the pipettes collect the sample sequentially one after another. In this non-limiting example all of the pipettes 60 collect a portion of the same sample. Optionally one or more pipettes collect a second sample, for instance an internal standard or other reference compound. In this example of operation, however, the plurality of delivery pipettes is utilized in order to enhance sensitivity by producing ions from one sample in parallel, i.e. simultaneously, and using FAIMS to deliver the ions of interest to a single orifice into the vacuum chamber of the mass spectrometer.

Figure 7:
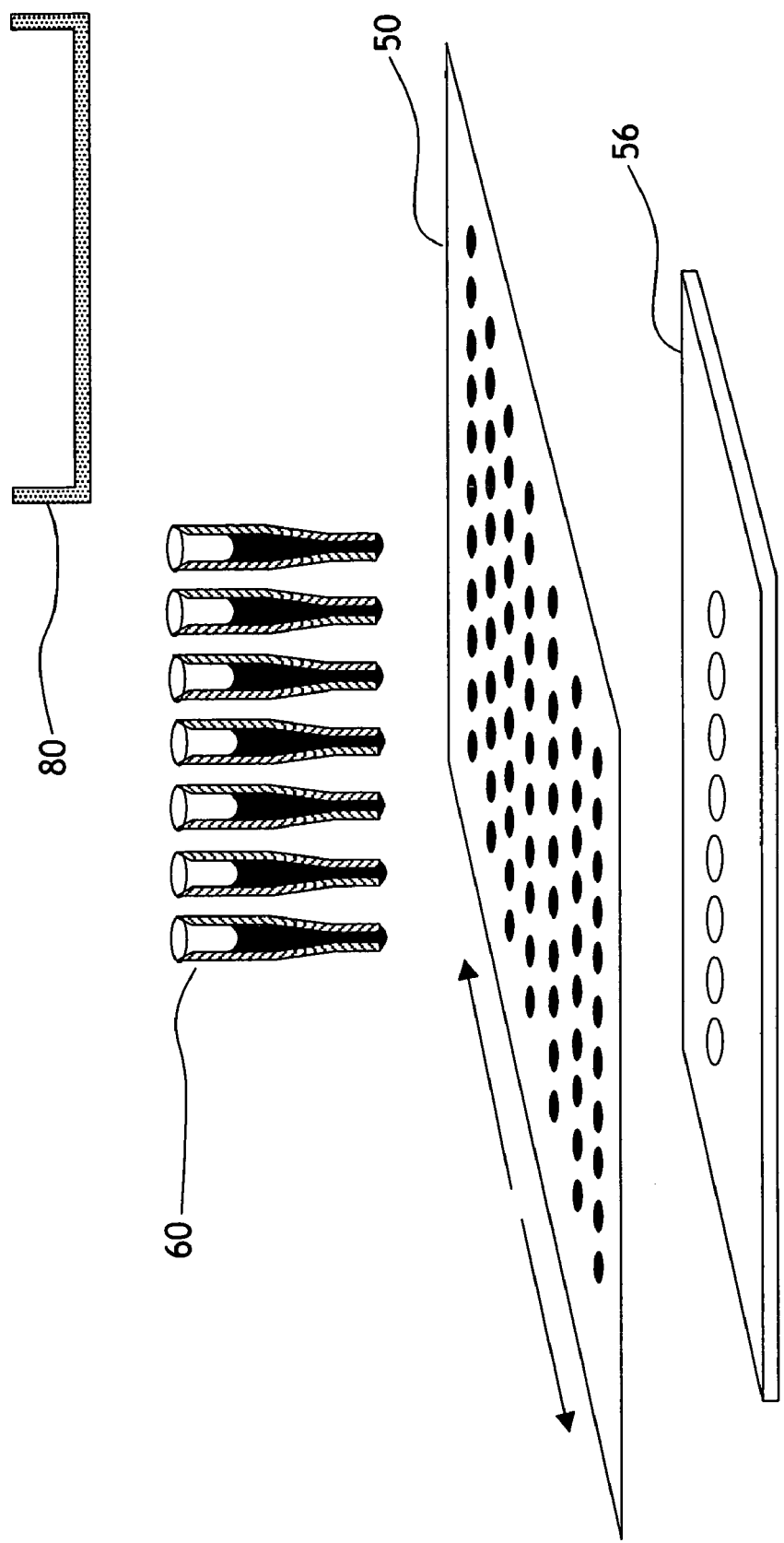
FIG. 7 is a simplified schematic diagram illustrating a second step of a method according to an embodiment of the instant invention.

In FIG. 7, the pipettes 60 are moved out of the sample reservoir 80 and toward the backside of the electrospray wafer 50. The pipettes are positioned so that the tip of each pipette is aligned with a corresponding capillary in the electrospray wafer 50.

Figure 8:
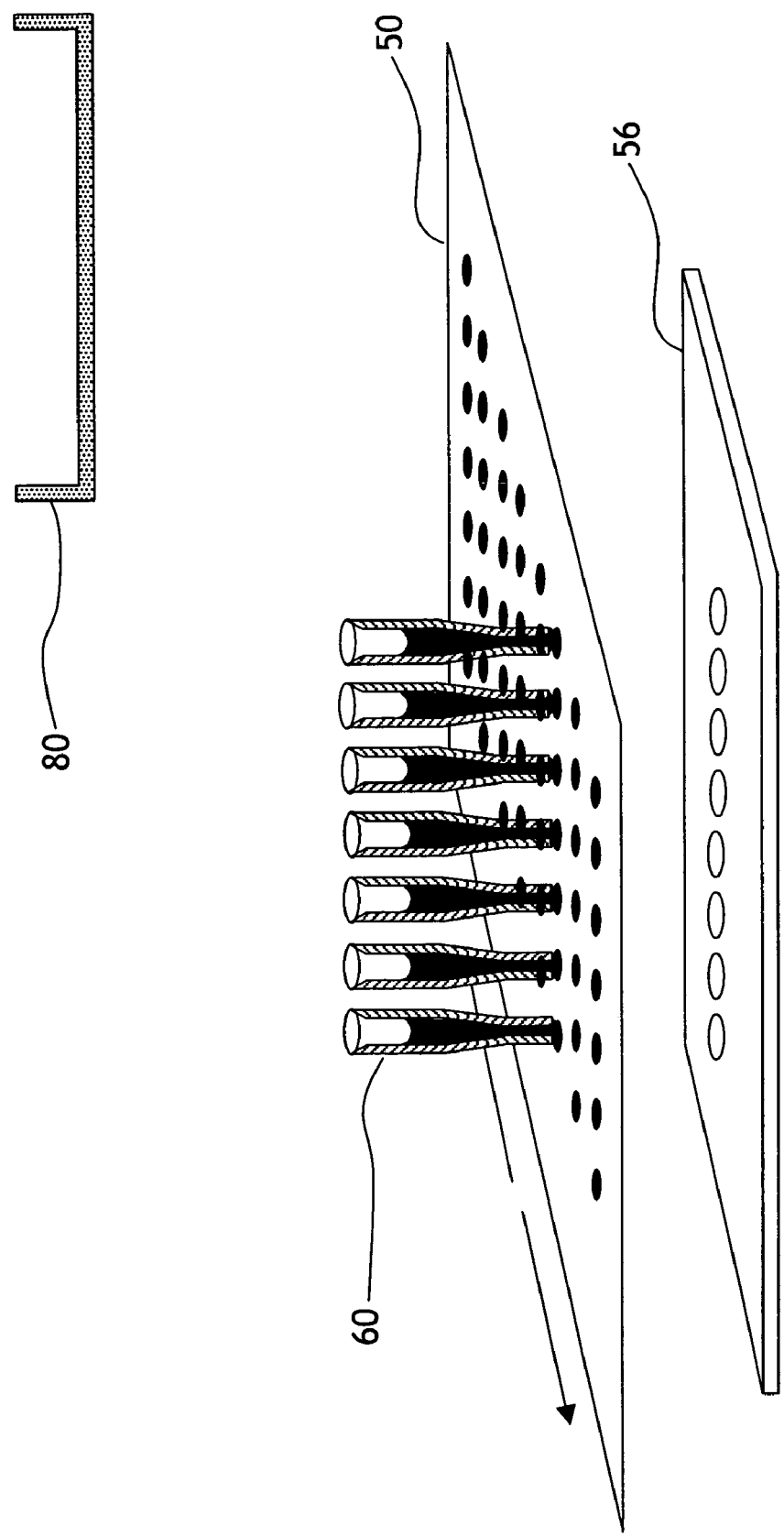
FIG. 8 is a simplified schematic diagram illustrating a third step of a method according to an embodiment of the instant invention.

FIG. 8 illustrates positioning of the pipette tips 60 in contact with the backside of the electrospray wafer 50. The liquid in the pipette tips is preferably pushed with a slight pressure of gas so that it flows out of the tip of the pipette and comes in contact with the capillary in the electrospray wafer 50. Capillary action now also starts to act to fill the length of the capillary with the sample.

Figure 9:
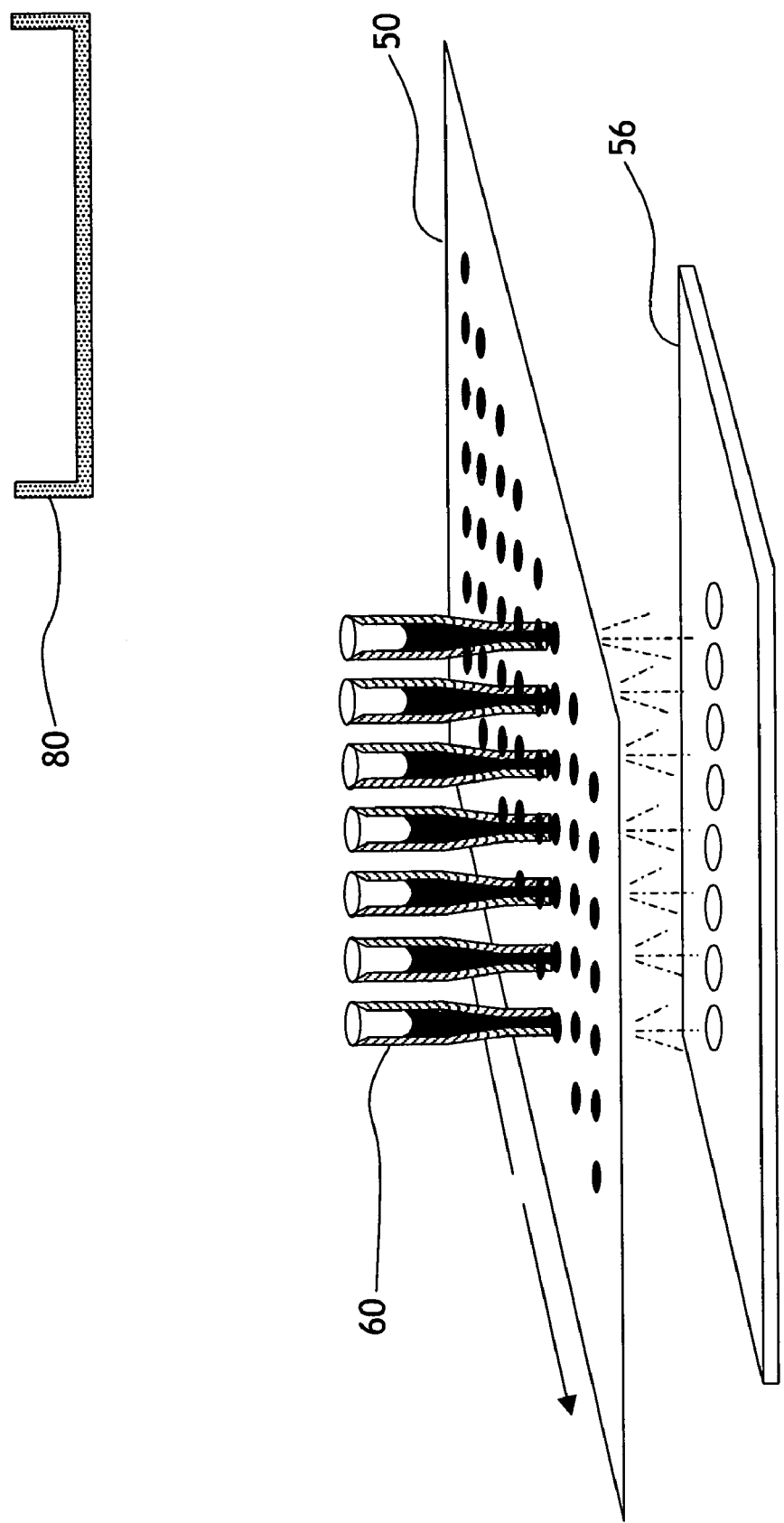
FIG. 9 is a simplified schematic diagram illustrating a fourth step of a method according to an embodiment of the instant invention.

FIG. 9 illustrates the electrospray ionization that occurs when voltage is applied either to the silicon wafer or to the sample liquid. The electrospray process is initiated optionally by application of voltage to the silicon wafer, if the wafer has sufficient conductivity, or by electrical contact to the sample directly, assuming the sample has sufficient electrical conductivity. Optionally, in the latter case the pipettes are prepared to have sufficient conductivity to accomplish this and electrical connection is made between the pipettes and a high voltage power supply. Since the electrical currents flowing in this system are below a microampere, the pipettes, sample and/or silicon wafer do not have to have very good conductivity to function as required to initiate the electrospray ionization process. By way of example the conductivity of the silicon electrospray wafer is enhanced by applying a surface coating of a conductive material.

Still referring to FIG. 9, it is an advantage of using multiple sprayers to ionize the same sample that failure of any one nozzle to operate properly does not lead to a failed sample run. The remaining nozzles deliver the sample to FAIMS and, other than a small decrease in the measured ion intensity, the analysis of the sample is successful.

Figure 10:
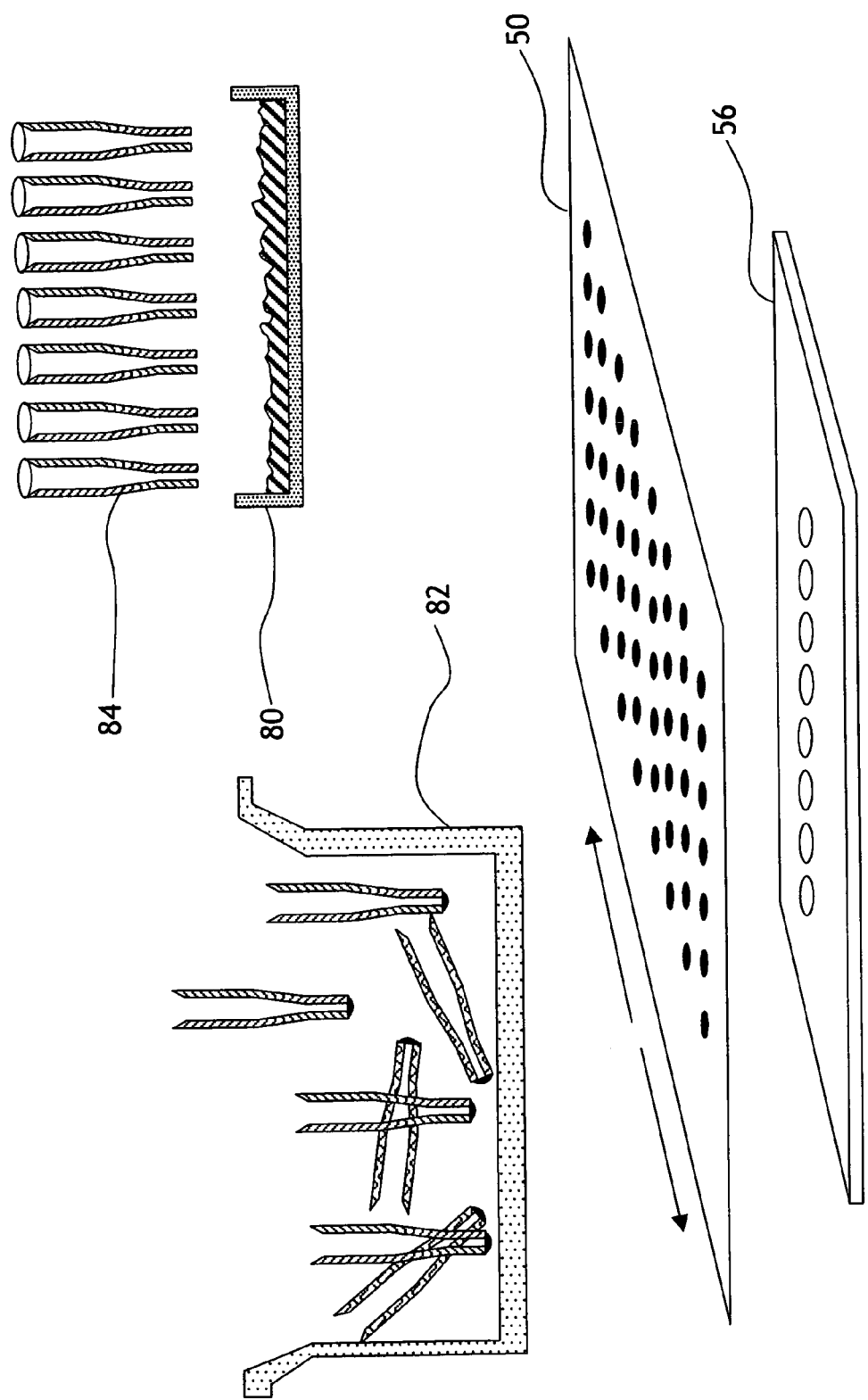
FIG. 10 is a simplified schematic diagram illustrating a fifth step of a method according to an embodiment of the instant invention.

Once the sample has been ionized as shown in FIG. 9, the set of pipettes 60 is discarded in an appropriate manner, for instance in a waste container 82 as shown in FIG. 10. The electrospray wafer 50 is translated in order to position a fresh set of nozzles in line with the openings in the curtain plate in preparation to ionize the next sample. A set of new pipettes 84 is prepared to collect the next sample. The process shown in FIGS. 6 to 10 is repeated through many cycles and optionally is automated.

Figures 11A, 11B, 11C, 11D:
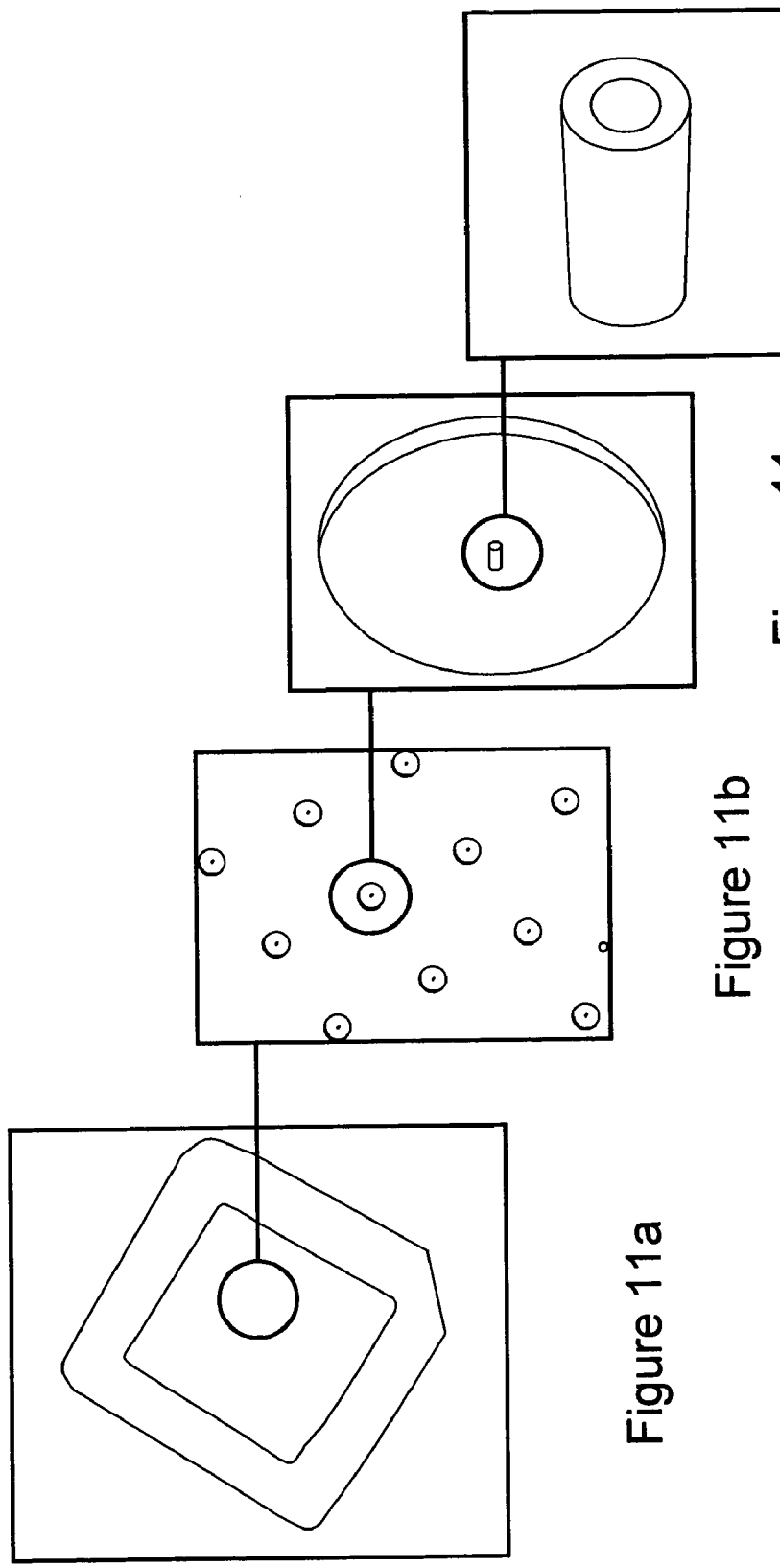
FIG. 11a shows an ESI Chip™.
FIG. 11b shows a first enlarged portion of the ESI Chip™, including a plurality of individual nozzles.
FIG. 11c shows a second enlarged portion of the ESI Chip™, including a single nozzle.
FIG. 11d shows a third enlarged portion of the ESI Chip™, including a capillary tube of a single nozzle.

FIG. 11a shows an example of a micro-machined silicon wafer with a plurality of identical nozzles suitable for electrospray ionization. FIG. 11b shows a first enlarged portion of the ESI Chip™ of FIG. 11a, including a plurality of individual nozzles. FIG. 11c shows a second enlarged portion of the ESI Chip™ of FIG. 11a, including a single nozzle. FIG. 11d shows a third enlarged portion of the ESI Chip™ of FIG. 11a, including a protruding tip of a single nozzle.

The ESI Chip™ shown in FIGS. 11a through 11d is fabricated and used by Advion Biosciences Inc. (Ithica, N.Y.) for an electrospray-based technology for sample delivery to a mass spectrometer. In practice one sample is delivered to one nozzle at a time. The nozzle is located adjacent to the orifice of a mass spectrometer, and the sample is ionized by the usual electrospray process. Since the mass spectrometer has a single small orifice it is not advantageous to simultaneously activate a plurality of the nozzles to obtain parallel ion plumes of a same sample loaded from a plurality of pipette tips. As a solution to this constraint, it is possible to locate a multitude of the nozzles in close proximity to each other so that a single pipette tip will deliver the same sample to several closely spaced capillaries and their respective nozzles. As noted above, the limitation is not the multiple spray capability of the electrospray wafer, but rather the single small orifice leading into the vacuum chamber of the mass spectrometer. It is this limitation that the FAIMS electrode system overcomes. Using FAIMS it is not necessary to design a system wherein the plurality of ion sprayers are assembled very closely together in an attempt to direct as many of the ions as possible into the single opening of the mass spectrometer.

Figure 12:
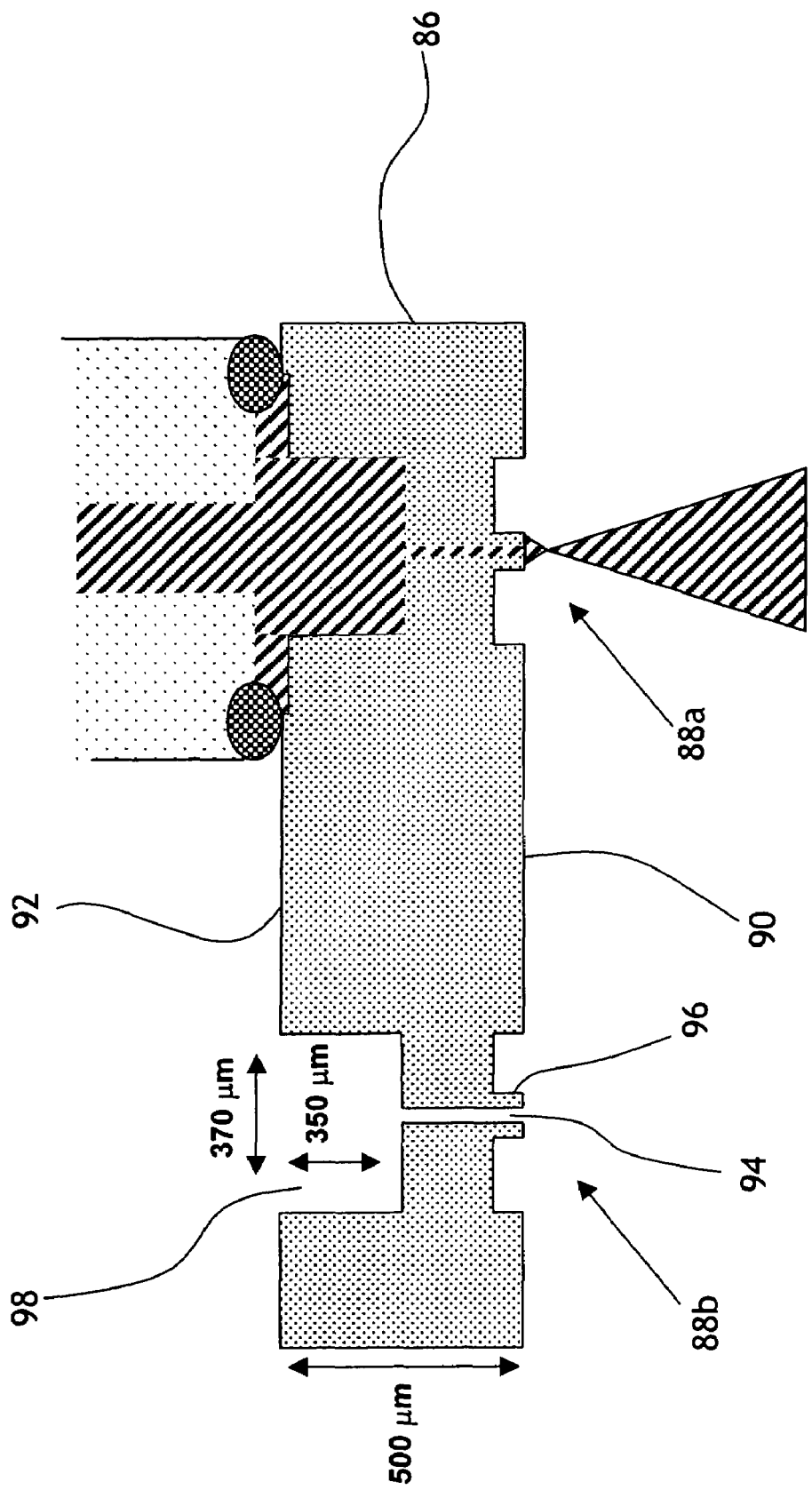
FIG. 12 shows a cross section view the capillary and nozzle system used in the Advion Biosciences version of ESI Chip™ technology.

FIG. 12 illustrates in cross section view the capillary and nozzle system used in the Advion Biosciences ESI chip™ technology. A substrate 86, for instance a monolithic silicon substrate, defines a plurality of electrospray nozzles 88a, 88b, etc. The substrate 86 has a front side 90 and a back side 92. Each nozzle, such as for instance nozzle 88a, is associated with a capillary tube 94, a protruding tip 96 and a small reservoir 98 located on the back side 92 of the silicon wafer. The pipette is placed in liquid-tight contact with the back side 92 of the silicon wafer and the sample is caused to flow into the reservoir 98 and into the capillary tube 94 leading to the protruding tip 96 of the nozzle. The liquid sprays out of the nozzle upon application of high voltage to the silicon wafer and/or the sample liquid. In this system, a new nozzle is used for every sample thus avoiding memory effects of the previous sample, degradation over time and clogging of the capillary tubes. The system is as reproducible as the fabrication of silicon wafers permits.

Figure 13A:
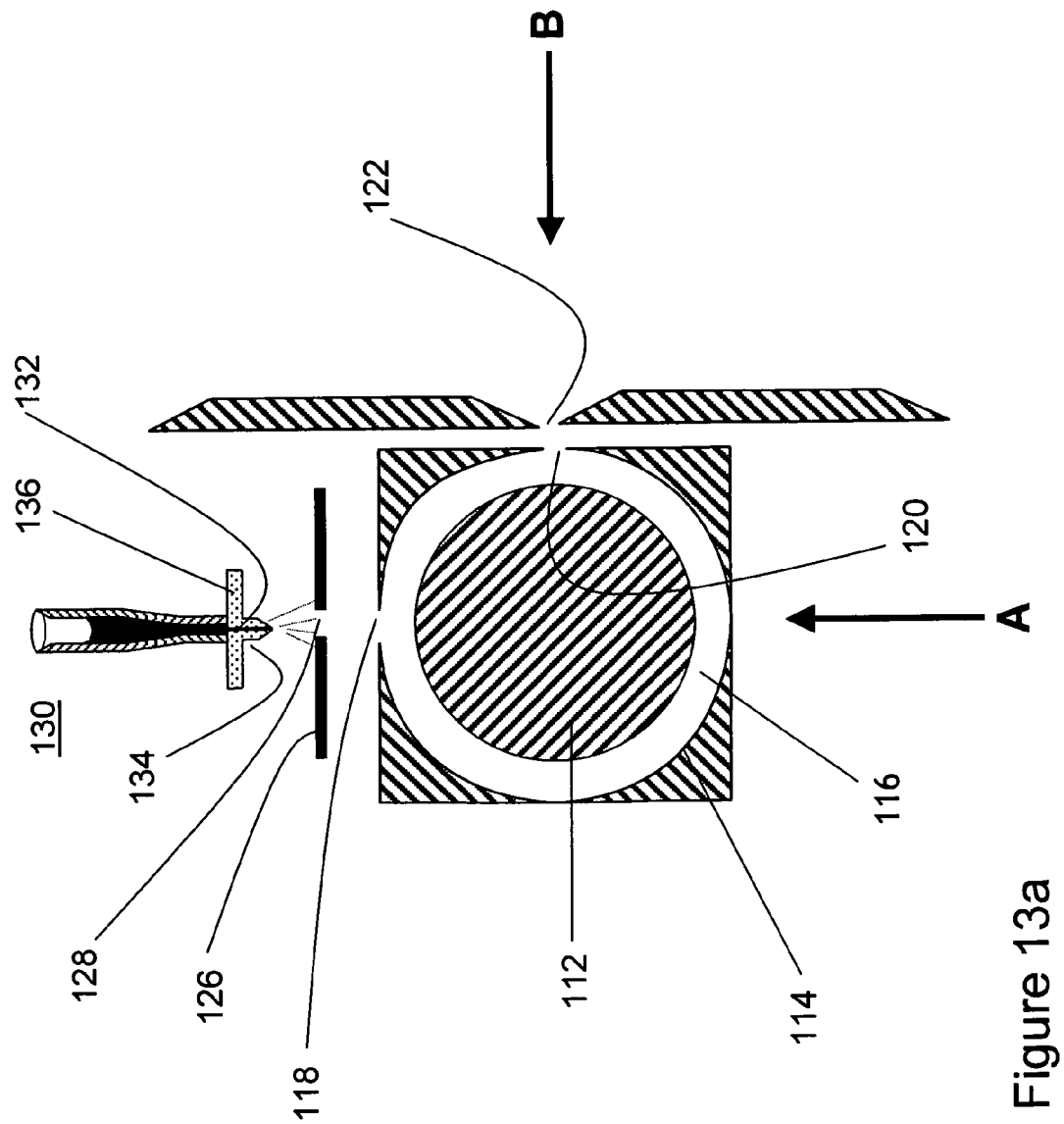
FIG. 13a shows a schematic diagram of an automated multiple sample spray system coupled with a side-to-side FAIMS system; and, FIG. 13b is a simplified cross-sectional view of the system of FIG. 13a taken along view AB.
Figure 13B:
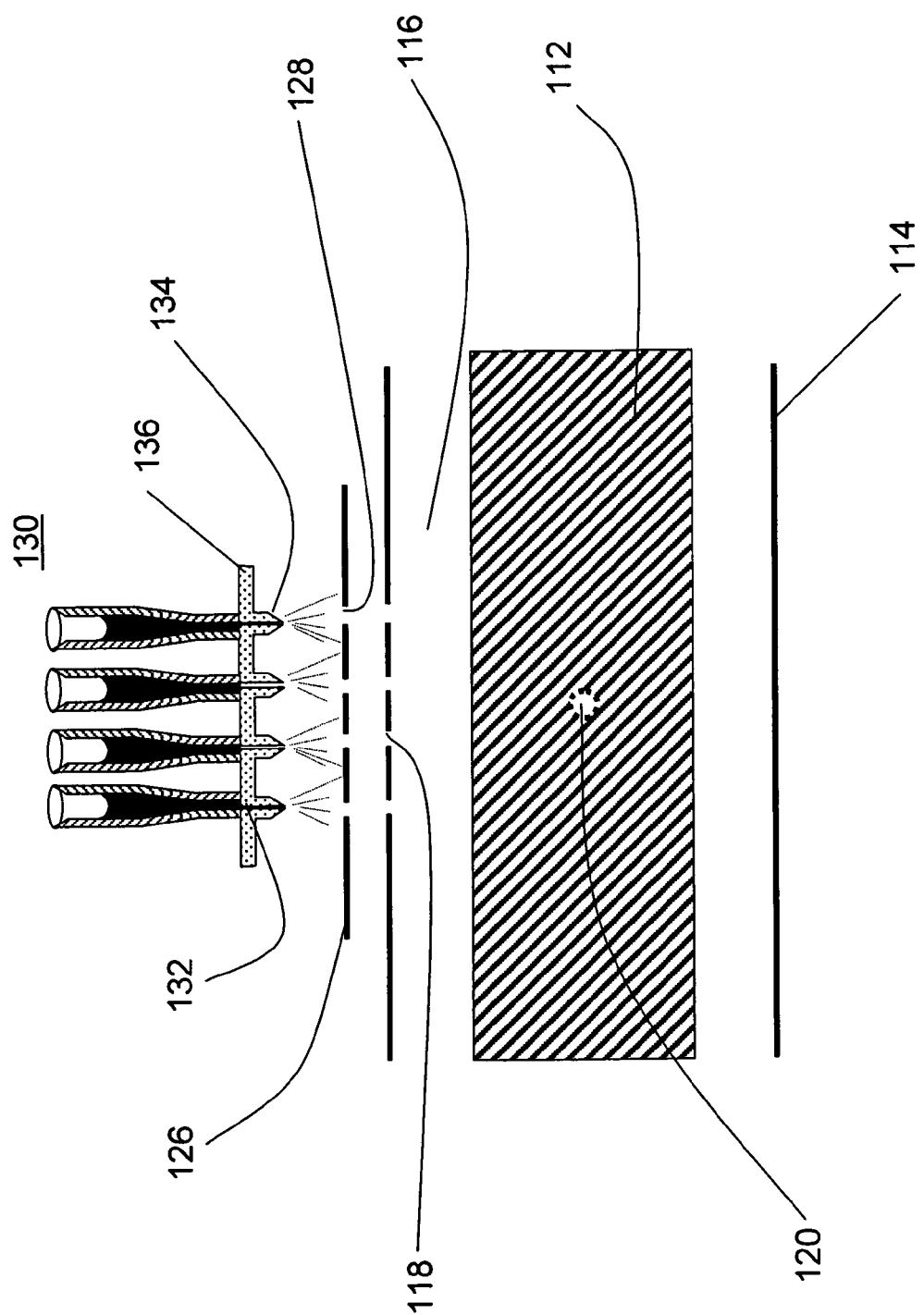

FIGS. 13a and 13b show an ion source, similar to that of FIG. 4, used with a side-to-side cylindrical geometry FAIMS. FIG. 13a is a simplified schematic diagram of an automated multiple sample spray system coupled with a side-to-side FAIMS system. An ionization source 130, for instance a micro-machined electrospray wafer 136 including a plurality of small capillaries 132 and protruding tips 134 is disposed adjacent to and spaced-apart from a curtain plate 126 of FAIMS. The small capillaries 132 and the protruding tips 134 are referred to simply as nozzles. In the interest of clarity, only one nozzle including one small capillary 132 and one protruding tip 134 is illustrated in FIG. 13a. Ions produced at different nozzles of the electrospray wafer 136 are driven by an electric field towards the curtain plate 126. Some of the sample ions pass through a plurality of openings 128 in the curtain plate 126. A voltage difference between the curtain plate 126 and the FAIMS outer electrode 114 directs the ions toward a plurality of ion inlets 118 defined through the FAIMS outer electrode 114. Hence, sample ions are introduced into different portions of the FAIMS analyzer region 116. Upon entering the analyzer region 116 background ions begin to collide with the surface of either the inner electrode 112 or the outer electrode 114, assuming appropriate conditions for selectively transmitting only the ions of interest are present. A flow of carrier gas "sweeps" the ions from the multiple ion inlets 118 to the single ion outlet 120 aligned with the orifice 122 of a not illustrated ion detection system. Similar to the embodiment of FIG. 4, space-charge repulsion and other inter-ion forces are reduced by introducing the sample ions via multiple ion inlets and allowing for some separation to occur before the ions of interest are combined in the ion stream exiting the FAIMS.

FIG. 13b is a cross-sectional view of the system of FIG. 13a taken along view AB. From FIG. 13b it is evident that ions introduced through the different ion inlets 118 have different shortest path lengths. The shortest path length is defined as the shortest distance an ion of interest travels as it is transmitted between the ion inlet where it was introduced and the single ion outlet. Referring still to FIG. 13b, optionally a mesh with an electrically conductive surface having perforations through which ions can pass is used in lieu of curtain plate 126 with multiple openings 128. Optionally, the plurality of ion inlets 118 defined through the FAIMS outer electrode 114 is a mesh as described above, mounted in the outer electrode 114.

Numerous other embodiments may be envisaged without departing from the spirit and scope of the invention.

What is claimed is:

1. An apparatus for separating ions, comprising:
a first electrode;
a second electrode that is spaced-apart from the first electrode so as to define a FAIMS analyzer region therebetween, the FAIMS analyzer region including a plurality of ion inlets defined through the first electrode for supporting fluid communication between the analyzer region and a region that is external to the analyzer region;
a micro-machined ionization source disposed within the region that is external to the analyzer region and including a plurality of spaced-apart nozzles, each nozzle of the plurality of spaced-apart nozzles being aligned approximately with an ion inlet of the plurality of ion inlets; and,
at least an electrical controller for applying an asymmetric waveform voltage and a direct current compensation voltage between the first electrode and the second electrode so as to generate an electrical field therebetween, and for applying a voltage for inducing ionization of a liquid sample that is provided to the micro-machined ionization source, wherein, during use, ions are provided simultaneously to different portions of the analyzer region via different ion inlets of the plurality of ion inlets, the ions provided through each ion inlet being produced substantially at a nozzle that is aligned approximately with that ion inlet.

2. An apparatus according to claim 1, comprising a curtain plate disposed between the micro-machined ionization source and the first electrode, the curtain plate including a plurality of openings defined therethrough, each opening of the plurality being aligned with a different nozzle of the plurality of spaced-apart nozzles for supporting ion flow therethrough.

3. An apparatus according to claim 1, wherein the micro-machined ionization source comprises a monolithic silicon wafer.

4. An apparatus according to claim 1, wherein the plurality of spaced-apart nozzles includes a plurality of rows of spaced-apart nozzles.

5. An apparatus according to claim 1, comprising a mechanism for translating a portion of the micro-machined ionization source between a first position in which each spaced-apart nozzle of the plurality of spaced apart nozzles is aligned approximately with an ion inlet of the plurality of ion inlets and a second position in which each spaced-apart nozzle of a different plurality of spaced apart nozzles is aligned approximately with an ion inlet of the plurality of ion inlets.

6. An apparatus according to claim 4, comprising a mechanism for translating the micro-machined ionization source between a first position in which a first row of spaced-apart nozzles is aligned approximately with the plurality of ion inlets and a second position in which a second row of the spaced-apart nozzles is aligned approximately with the plurality of ion inlets.

7. An apparatus according to claim 1, comprising a sample loader including a plurality of sample containing vessels for providing a sample from a reservoir to each spaced-apart nozzle of the plurality of spaced-apart nozzles.

8. An apparatus according to claim 7, wherein the sample loader comprises a plurality of disposable pipette tips.

9. An apparatus according to claim 1, wherein the at least an electrical controller comprises a first electrical controller for applying the asymmetric waveform voltage and the direct current compensation voltage between the first electrode and the second electrode, and a second electrical controller for applying the voltage for inducing ionization of the liquid sample.

10. An apparatus according to claim 9, comprising an electrical contact on the micro-machined ionization source for receiving the voltage from the second electrical controller.

11. An apparatus according to claim 9, comprising an electrical contact that, during use, is in communication with the liquid sample that is provided to the micro-machined ionization source, for receiving the voltage from the second electrical controller.

12. An apparatus for separating ions, comprising:
an ionization source comprising a substrate defining a plurality of discrete nozzles, each discrete nozzle having a first end for receiving a liquid sample including a species of interest, a second end for providing a flow of a fluid including ions of the species of interest, and a passageway defined through the substrate and extending between the first end and the second end for conducting the liquid sample between the first end and the second end;
an electrical contact on the ionization source for receiving an electrical signal, the electrical signal for use in producing ions from the liquid sample that is contained within the passageways of at least some of the plurality of discrete nozzles; and, a FAIMS analyzer comprising an analyzer region defined between two spaced-apart electrodes and including an ion outlet and a plurality of ion inlets, each ion inlet of the plurality of ion inlets being defined at a different distance from the ion outlet such tat, during use, a mixture of ions introduced via a first ion inlet is partially separated prior to mixing with a mixture of ions introduced via a second ion inlet that is disposed between the first ion inlet and the ion outlet.

13. An apparatus according to claim 12, wherein the ionization source is a micro-machined ionization source fabricated from a monolithic substrate.

14. An apparatus according to claim 13, wherein the monolithic substrate is a silicon containing substrate.

15. An apparatus according to claim 12, wherein the plurality of discrete nozzles comprises a plurality of rows of spaced-apart nozzles.

16. An apparatus according to claim 12, comprising a curtain plate disposed between the ionization source and the FAIMS analyzer, the curtain plate including a plurality of openings defined therethrough, each opening of the plurality being aligned with a different discrete nozzle of the plurality of discrete nozzles for supporting ion flow therethrough.

17. An apparatus for separating ions, comprising:

an ionizer comprising a monolithic substrate defining a plurality of discrete ionization sources that are disposed in a predetermined spaced-apart arrangement;

a FAIMS analyzer comprising an analyzer region defined between two spaced-apart electrodes and including an ion outlet and a plurality of ion inlets, the plurality of ion inlets being arranged in the predetermined spaced-apart arrangement, such that each ion inlet is aligned with one of the plurality of discrete ionization sources when in an assembled condition; and, an electrical contact on the ionizer for receiving an electrical signal for initiating ionization of a liquid sample that is provided to the ionizer, so as to provide simultaneously ions from each of the plurality of discrete ionization sources.

18. An apparatus according to claim 17, wherein the ionization source is a micro-machined ionization source.

19. An apparatus according to claim 18, wherein the monolithic substrate is a monolithic silicon substrate.

20. An apparatus according to claim 17, wherein each discrete ionization source of the ionizer is a nozzle comprising a capillary passageway defined through the monolithic substrate and open at both ends thereof, and a protruding tip for directing ions toward an ion inlet of the plurality of ion inlets of the FAIMS analyzer.

21. A method for separating ions, comprising:

providing a FAIMS analyzer region defined between a first electrode and a second electrode;

applying an asymmetric waveform voltage and a direct current compensation voltage between the first electrode and the second electrode to generate an electric field within the analyzer region;

providing a liquid sample to each of a plurality of discrete nozzles of an ionizer, each discrete nozzle being defined by a separate passageway extending through a substrate of the ionizer;

applying a voltage to the ionizer for effecting ionization of the liquid sample at each discrete nozzle, to produce ions of species that are contained within the liquid sample;

during a same overlapping period of time, introducing ions produced at each discrete nozzle through a corresponding ion inlet of a plurality of ion inlets into the FAIMS analyzer region, such that ions produced at each discrete nozzle are introduced into a different volume of the FAIMS analyzer region via a different ion inlet of the plurality of ion inlets; and, selectively transmitting ions of a same type introduced through each ion inlet of the plurality of ion inlets toward a same ion outlet from the FAIMS analyzer region, such that ions introduced via different ion inlets have different residence times within the FAIMS analyzer region.

22. A method according to claim 21, wherein selectively transmitting ions comprises introducing a flow of a carrier gas through the FAIMS analyzer region and out through the ion outlet.

23. A method according to claim 21, comprising detecting the selectively transmitted ions using an ion detection system that is disposed external to the FAIMS analyzer region.

* * * * *

UNITED STATES PATENT AND TRADEMARK OFFICE
CERTIFICATE OF CORRECTION

PATENT NO. : 7,265,347 B2  Page 1 of 1
APPLICATION NO. : 11/130124
DATED : September 4, 2007
INVENTOR(S) : Guevremont et al.

It is certified that error appears in the above-identified patent and that said Letters Patent is hereby corrected as shown below:

In the claims:
Column 13, claim 12, line 8
The word "tat" should be replaced with --that--

Signed and Sealed this

Eleventh Day of December, 2007

JON W. DUDAS
*Director of the United States Patent and Trademark Office*